US011896286B2

(12) United States Patent
Gliner et al.

(10) Patent No.: US 11,896,286 B2
(45) Date of Patent: Feb. 13, 2024

(54) MAGNETIC AND OPTICAL CATHETER ALIGNMENT

(71) Applicant: BIOSENSE WEBSTER (ISRAEL) LTD., Yokneam (IL)

(72) Inventors: Vadim Gliner, Haifa (IL); Assaf Govari, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 1033 days.

(21) Appl. No.: 16/536,720

(22) Filed: Aug. 9, 2019

(65) Prior Publication Data

US 2021/0038284 A1 Feb. 11, 2021

(51) Int. Cl.

| | |
|---|---|
| ***A61B 18/14*** | (2006.01) |
| ***A61B 5/06*** | (2006.01) |
| ***G06T 7/00*** | (2017.01) |
| *A61B 34/20* | (2016.01) |

(52) U.S. Cl.

CPC .............. *A61B 18/14* (2013.01); *A61B 5/062* (2013.01); *G06T 7/0012* (2013.01); *A61B 2034/2051* (2016.02); *A61B 2560/0233* (2013.01); *A61B 2562/0223* (2013.01); *G06T 2207/30021* (2013.01)

(58) Field of Classification Search

None

See application file for complete search history.

(56) References Cited

U.S. PATENT DOCUMENTS

| | | | |
|---|---|---|---|
| 5,391,199 | A | 2/1995 | Ben-Haim |
| 6,239,724 | B1 | 5/2001 | Doron et al. |
| 6,266,551 | B1 | 7/2001 | Osadchy et al. |
| 6,332,089 | B1 | 12/2001 | Acker et al. |
| 6,427,314 | B1 | 8/2002 | Acker |
| 6,584,118 | B1 | 6/2003 | Russell et al. |
| 6,618,612 | B1 | 9/2003 | Acker et al. |

(Continued)

FOREIGN PATENT DOCUMENTS

| | | |
|---|---|---|
| WO | WO 1996/005768 | 2/1996 |
| WO | WO 2018/232322 | 12/2018 |

OTHER PUBLICATIONS

International Search Report dated Nov. 5, 2020 from corresponding PCT Patent Application No. PCT/IB2020/057399.

(Continued)

*Primary Examiner* — Douglas X Rodriguez
(74) *Attorney, Agent, or Firm* — Frost Brown Todd LLP

(57) ABSTRACT

In one embodiment, an apparatus for calibrating a probe that includes an image sensor and a magnetic field sensor, includes a jig configured to hold the probe, a magnetic field generator configured to generate at least one magnetic field having a predefined direction in alignment with the jig, an optical target aligned with the jig so that the image sensor in the probe is able to capture an image of the optical target while the probe is held in the jig, and processing circuitry configured to receive from the probe a signal output by the magnetic field sensor in response to the at least one magnetic field and the image captured by the image sensor while the probe is held in the jig, and to calibrate an alignment of the image sensor relative to the magnetic field sensor responsively to the received signal and the received image.

21 Claims, 11 Drawing Sheets

40
40
30
40
36
46
Y
Z
10,12
38
44
X
PROCESSING CIRCUITRY
40
34

(56) References Cited

U.S. PATENT DOCUMENTS

| | | | | |
|---|---|---|---|---|
| 6,690,963 | B2 | 2/2004 | Ben Haim et al. | |
| 2003/0120150 | A1 | 6/2003 | Govari | |
| 2004/0068178 | A1 | 4/2004 | Govari | |
| 2006/0058647 | A1 | 3/2006 | Strommer et al. | |
| 2008/0183075 | A1* | 7/2008 | Govari | A61B 8/587 600/437 |
| 2013/0281821 | A1 | 10/2013 | Liu et al. | |
| 2014/0028819 | A1* | 1/2014 | Nakano | A61B 1/00057 348/E17.002 |
| 2015/0313503 | A1 | 11/2015 | Seibel et al. | |
| 2019/0044784 | A1 | 2/2019 | Cohen et al. | |
| 2021/0145254 | A1* | 5/2021 | Shekhar | G02B 23/2453 |

OTHER PUBLICATIONS

Hoffman, Mathis et al., "A Robust Chessboard Detector for Geometric Camera Calibration," Fraunhofer Institute for Integrated Circuits IIS, Proceedings of the 12$^{th}$ International Joint Conference on Computer Vision, Imaging and Computer Graphics Theory and Applications (VISGRAPP 2017 pp. 34-43.

* cited by examiner

Z
X
Y
44

54
48
46
56

X
Y
44

MAGNETIC AND OPTICAL CATHETER ALIGNMENT

FIELD OF THE INVENTION

The present invention relates to optical alignment of a probe.

BACKGROUND

A wide range of medical procedures involve placing probes, such as guidewires and catheters, within a patient's body. Location sensing systems have been developed for tracking such probes. Magnetic location sensing is one of the methods known in the art. In magnetic location sensing, magnetic field generators are typically placed at known locations external to the patient. A magnetic field sensor within the distal end of the probe generates electrical signals in response to these magnetic fields, which are processed to determine the coordinate locations of the distal end of the probe. These methods and systems are described in U.S. Pat. Nos. 5,391,199, 6,690,963, 6,484,118, 6,239,724, 6,618,612 and 6,332,089, in PCT International Publication No. WO 1996/005768, and in U.S. Patent Application Publications Nos. 2003/0120150, issued as U.S. Pat. No. 7,729,742 on Jun. 1, 2020, and 2004/0068178, now abandoned, whose disclosures are all incorporated herein by reference.

U.S. Pat. No. 6,266,551 (hereinafter the '551 patent) to Osadchy, et al., which is herein incorporated by reference, describes a probe for insertion into the body of a subject, the probe having distal and proximal ends, and including an electronic microcircuit, which stores information relating to calibration of the probe. Preferably, the microcircuit stores a calibration code, which is encrypted. Alternatively, or additionally, the microcircuit stores a usage code, which controls availability of the probe to a user thereof. The probe includes access control circuitry that allows the usage code to be changed so as to reduce the availability of the probe, but not to increase the availability thereof.

The '551 patent describes that systems for electromagnetic detection of catheter position and orientation are generally located in the catheter at a small distance proximal to the catheter's distal tip, since the distal tip is typically occupied by an electrode or other functional element. Therefore, the position and orientation detection system needs to be calibrated to take into account the displacement of the distal tip of the catheter relative to the location of the coils. Because of manufacturing variations, this displacement generally varies from one catheter to another. Furthermore, the coils used to generate position signals may not be precisely orthogonal. For purposes of computing the position and orientation of the catheter, the axes of the coils define the respective axes of a coordinate system that is fixed to the catheter tip, and the directions of these axes must be known relative to the catheter. If these axes deviate from orthogonality, the respective degrees of deviation must be known and corrected for in the position and orientation computation. Additionally, the relative gains of the coils determine the strengths of the respective position signals that the coils generate in response to externally-applied fields. Since these signal strengths are used in computing the position and orientation of the catheter, deviations of the gains from their expected values will lead to inaccuracy in the computed position and orientation. Therefore, the respective gains of the coils must be known and corrected for in the position and orientation computation.

The '551 patent provides a method of calibrating a device that is used to determine the position and orientation of a catheter, wherein the calibration information is retained in the catheter. The calibration information is stored digitally in a microcircuit whose location is easily accessible to signal processing circuits and computing apparatus, so that the catheter need not contain digital signal wires, and so that digital electronic signals transmitted from the microcircuit to the signal processing circuits and computing apparatus do not interfere with low-level analog signals conveyed by wires from the distal end of the catheter to the circuits.

The '551 patent describes a device used to determine the position and orientation of a catheter inside the body. The device, such as a Helmholtz Calibration Chamber, comprises a plurality of coils adjacent to the distal end of the catheter. The catheter further comprises an electronic microcircuit adjacent to the proximal end of the catheter. The microcircuit stores information relating to the calibration of the device.

U.S. Pat. No. 6,427,314 to Acker describes a magnetic position and orientation determining system that uses magnetic fields, desirably including uniform fields from Helmholtz coils positioned on opposite sides of a sensing volume and gradient fields generated by the same coils. By monitoring field components detected at the probes during application of these fields, the position and orientation of the probe in the field can be deduced. A representation of the probe can be superposed on a separately acquired image of the subject to show the position and orientation of the probe with respect to the subject.

US Patent Publication 2019/0044784 of Cohen, et al., issued as U.S. Pat. No. 10,917,281 on Feb. 9, 2021, describes an apparatus for displaying a moving region of interest located within a body includes a positioning system to determine a position and orientation (P&O) of a medical device as well as to track, using an internal position reference sensor, the motion of the region of interest over time. A compensation function block generates a motion compensation function based on the motion of the region of interest, which is configured to compensate for the motion of the region of interest between a first time, for example a time at which an image was acquired and a second time, for example a time at which a P&O of the device was measured. The measured P&O is corrected using the compensation function. A representation of the medical device is superimposed on the image in accordance with the corrected P&O.

US Patent Publication 2006/0058647 of Strommer, et al., issued as U.S. Pat. No. 8,442,618 on May 14, 2013, describes a method for delivering a medical device coupled with a catheter, to a selected position within a lumen of the body of a patient, the method comprising the procedures of: registering a three-dimensional coordinate system with a two-dimensional coordinate system, the three-dimensional coordinate system being associated with a medical positioning system (MPS), the two-dimensional coordinate system being associated with a two-dimensional image of the lumen, the two-dimensional image being further associated with an organ timing signal of an organ of the patient; acquiring MPS data respective of a plurality of points within the lumen, each of the points being associated with the three-dimensional coordinate system, each of the points being further associated with a respective activity state of the organ; determining a temporal three-dimensional trajectory representation for each the respective activity states from the acquired MPS data which is associated with the respective activity state; superimposing the temporal three-dimensional trajectory representations on the two-dimensional image, according to the respective activity state; receiving position data respective of the selected position, by selecting at least one of the points along the temporal three-dimensional trajectory representation; determining the coordinates of the selected position in the three-dimensional coordinate system, from the selected at least one point; determining the current position of the medical device in the three-dimensional coordinate system, according to an output of an MPS sensor attached to the catheter in the vicinity of the medical device; maneuvering the medical device through the lumen, toward the selected position, according to the current position relative to the selected position; and producing a notification output when the current position substantially matches the selected position.

SUMMARY

There is provided in accordance with an embodiment of the present disclosure, an apparatus for calibrating a probe that includes an image sensor and a magnetic field sensor, the apparatus including a jig configured to hold the probe, a magnetic field generator configured to generate at least one magnetic field having a predefined direction in alignment with the jig, an optical target aligned with the jig so that the image sensor in the probe is able to capture an image of the optical target while the probe is held in the jig, and processing circuitry configured to receive from the probe a signal output by the magnetic field sensor in response to the at least one magnetic field and the image captured by the image sensor while the probe is held in the jig, and to calibrate an alignment of the image sensor relative to the magnetic field sensor responsively to the received signal and the received image.

Further in accordance with an embodiment of the present disclosure the processing circuitry is configured to calibrate an alignment of the magnetic field sensor to the at least one magnetic field generated by the magnetic field generator responsively to the received signal.

Still further in accordance with an embodiment of the present disclosure the processing circuitry is configured to store the alignment of the image sensor relative to the magnetic field sensor and the alignment of the magnetic field sensor to the at least one magnetic field in a storage device included in the probe.

Additionally, in accordance with an embodiment of the present disclosure the processing circuitry is configured to compute a sensitivity of the magnetic field sensor responsively to the received signal.

Moreover in accordance with an embodiment of the present disclosure the optical target includes multiple alignment features, the received image includes at least some alignment features of the multiple alignment features, and the processing circuitry is configured to compute an optical-aberration correction for the image sensor responsively to respective positions of respective ones of the at least some alignment features in the received image.

Further in accordance with an embodiment of the present disclosure the processing circuitry is configured to compute the optical-aberration correction for the image sensor responsively to a curvature of at least one line defined by the respective positions of respective ones of the at least some alignment features in the received image.

Still further in accordance with an embodiment of the present disclosure the optical target includes multiple alternating rectangular sections, and the processing circuitry is configured to find respective boundaries between respective ones of the rectangular sections corresponding with respective ones of the multiple alignment features.

Additionally in accordance with an embodiment of the present disclosure a central boundary between ones of the rectangular sections corresponds with a central alignment feature of the multiple alignment features, the processing circuitry being configured to calibrate the alignment of the image sensor relative to the magnetic field sensor responsively to the position of the central alignment feature in the received image.

Moreover in accordance with an embodiment of the present disclosure the optical target is configured to be rotated around the central alignment feature, and the processing circuitry is configured to receive a plurality of respective images captured by the image sensor of the optical target at multiple respective rotational positions of the optical target, and compute the optical-aberration correction for the image sensor responsively to the respective positions of respective ones of the at least some alignment features in the respective received images.

Further in accordance with an embodiment of the present disclosure the magnetic field generator includes three calibration-coil sets respectively aligned with three orthogonal axes of a magnetic coordinate frame, the magnetic field sensor includes three position coils, and the processing circuitry is configured to actuate the calibration-coil sets to generate magnetic fields for detection by the position coils, and calibrate, for each of the position coils, an alignment with the magnetic coordinate frame responsively to signals received from position coils.

Still further in accordance with an embodiment of the present disclosure each of the calibration-coil sets is a Helmholtz coil.

There is also provided in accordance with another embodiment of the present disclosure, a method for calibrating a probe that includes an image sensor and a magnetic field sensor, the method including disposing the probe in a jig, generating at least one magnetic field having a predefined direction in alignment with the jig, capturing with the image sensor an image of an optical target aligned with the jig while the probe is held in the jig, receiving from the probe a signal output by the magnetic field sensor in response to the at least one magnetic field and the image captured by the image sensor while the probe is held in the jig, and calibrating an alignment of the image sensor relative to the magnetic field sensor responsively to the received signal and the received image.

Additionally, in accordance with an embodiment of the present disclosure, the method includes calibrating an alignment of the magnetic field sensor to the at least one magnetic field responsively to the received signal.

Moreover, in accordance with an embodiment of the present disclosure, the method includes storing the alignment of the image sensor relative to the magnetic field sensor and the alignment of the magnetic field sensor to the at least one magnetic field in a storage device included in the probe.

Further in accordance with an embodiment of the present disclosure, the method includes computing a sensitivity of the magnetic field sensor responsively to the received signal.

Still further in accordance with an embodiment of the present disclosure the optical target includes multiple alignment features, the received image includes at least some alignment features of the multiple alignment features, and the method further including computing an optical-aberration correction for the image sensor responsively to respective positions of respective ones of the at least some alignment features in the received image.

Additionally, in accordance with an embodiment of the present disclosure the computing of the optical-aberration correction is performed responsively to a curvature of at least one line defined by the respective positions of respective ones of the at least some alignment features in the received image.

Moreover, in accordance with an embodiment of the present disclosure the optical target includes multiple alternating rectangular sections, and the method further includes finding respective boundaries between respective ones of the rectangular sections corresponding with respective ones of the multiple alignment features.

Further in accordance with an embodiment of the present disclosure a central boundary between ones of the rectangular sections corresponds with a central alignment feature of the multiple alignment features, the calibrating the alignment of the image sensor relative to the magnetic field sensor is performed responsively to the position of the central alignment feature in the received image.

Still further in accordance with an embodiment of the present disclosure, the method includes rotating the optical target around the central alignment feature to multiple rotational positions, receiving a plurality of respective images captured by the image sensor of the optical target at respective ones of the multiple rotational positions of the optical target, and wherein the computing the optical-aberration correction for the image sensor is performed responsively to the respective positions of respective ones of the at least some alignment features in the respective received images.

Additionally in accordance with an embodiment of the present disclosure, the method includes actuating three calibration-coil sets respectively aligned with three orthogonal axes of a magnetic coordinate frame to generate magnetic fields for detection by three position coils of the magnetic field sensor, and calibrating, for each of the position coils, an alignment with the magnetic coordinate frame responsively to signals received from position coils.

BRIEF DESCRIPTION OF THE DRAWINGS

The present invention will be understood from the following detailed description, taken in conjunction with the drawings in which.

DESCRIPTION OF EXAMPLE EMBODIMENTS

Overview

Figure 1:
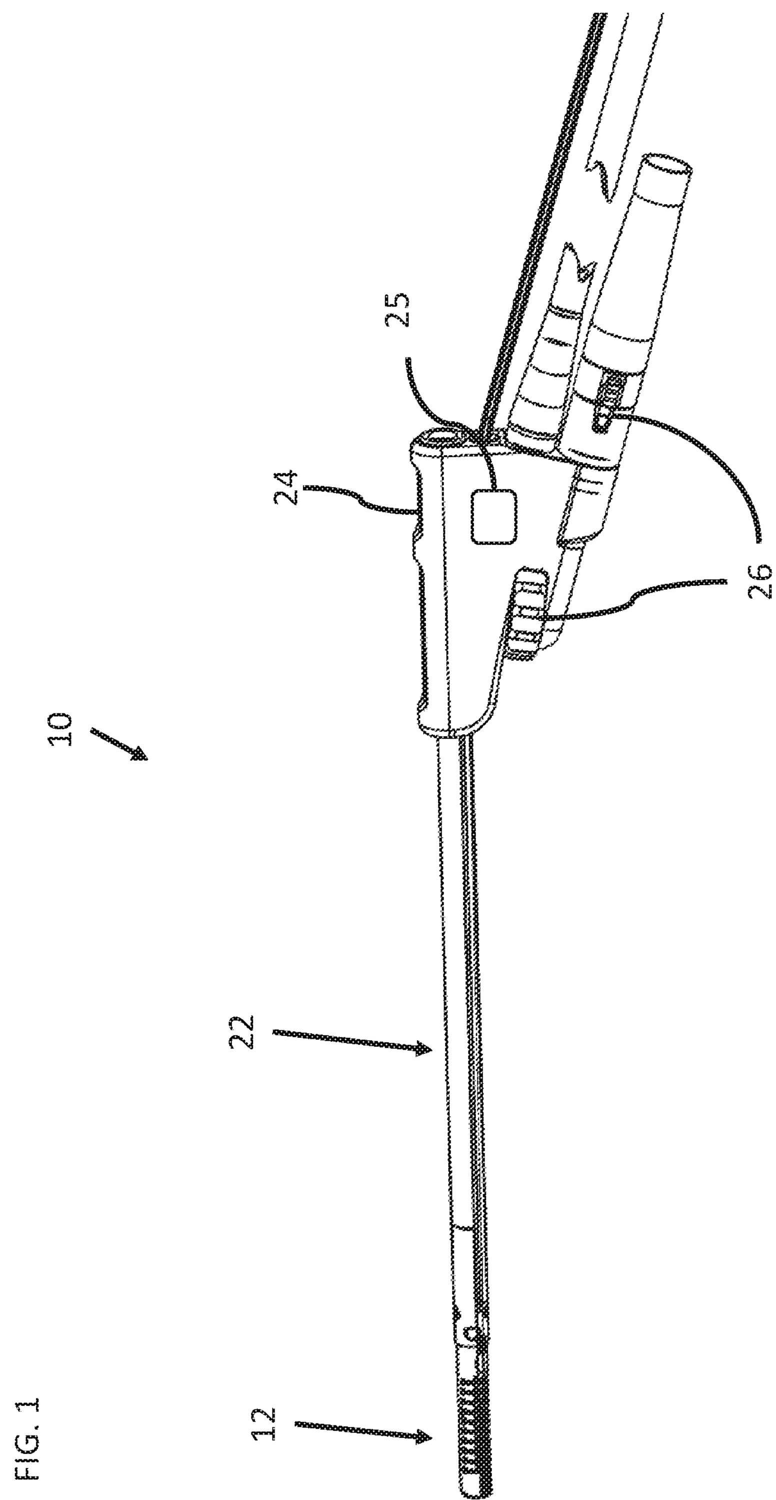
FIGS. 1-3 are schematic views of a probe constructed and operative in accordance with an embodiment of the present invention.

For a probe (such as a catheter, guidewire, or a medical tool, e.g., an ENT tool) having an image sensor (e.g., a camera) and a magnetic-field sensor, both the image sensor and the magnetic-field sensor may need to be aligned with the axis of the probe, or alternatively any misalignment may need to be compensated for by calibration. The need for alignment or calibration generally stems from inaccuracies incorporated during manufacture of the probe, especially if the probe is manually assembled. It should be noted that for the image sensor even a small misalignment might lead to relatively large errors in registering the image sensor image, for example, when the image is displayed along-side, or superimposed on, a different image (e.g., CT, MRI, or ultrasound image) of the same body part.

One solution is to calibrate the magnetic-field sensor in a magnetic-field calibration apparatus such as the calibration device described in the '551 patent and to separately calibrate the image sensor in an optical calibration device, for example, by placing the probe in a jig which has a fixed orientation with an optical target and analyzing images captured by the image sensor to determine an alignment correction for the image sensor. This separate calibration is time consuming and error-prone due to discrepancies between the two calibration devices.

Embodiments of the present invention solve the above problems by providing an apparatus that combines calibration of the image sensor and the magnetic-field sensor while the probe is being held in the same jig.

A magnetic field generator generates at least one time-varying magnetic field having a predefined direction in alignment with the jig. An optical target is aligned with the jig so that the image sensor in the probe is able to capture an image of the optical target while the probe is held in the jig. Processing circuitry receives from the probe a signal (or signals) output by the magnetic field sensor in response to the magnetic field(s) and the image captured by the image sensor while the probe is held in the jig. The processing circuitry calibrates an alignment of the image sensor relative to the magnetic field sensor responsively to the received signal(s) and the received image. The processing circuitry also calibrates an alignment of the magnetic field sensor to the magnetic field(s) generated by the magnetic field generator responsively to the received signal(s).

In some embodiments, the optical target comprises multiple alignment features such as alternating rectangular sections, e.g., alternating black and white squares, similar to a chess or checkers board. Therefore, the image received from the image sensor includes at least some of the multiple alignment features, and the processing circuitry finds respective boundaries between the respective rectangular sections corresponding with the respective alignment features. A central boundary, between the rectangular sections at the center of the optical target, corresponds with a central alignment feature, and the processing circuitry calibrates the alignment of the image sensor relative to the magnetic field sensor responsively to the position of the central alignment feature and/or other features in the received image.

In some embodiments, the processing circuitry computes an optical-aberration correction (spherical and/or chromatic aberration) for the image sensor responsively to respective positions of the respective alignment features in the received image. The processing circuitry computes the optical-aberration correction for the image sensor responsively to the curvature of a line or lines defined by the respective positions of the respective alignment features in the received image.

In some embodiments, the optical target is configured to be rotated around the central alignment feature of the alignment features, e.g., a central intersection of the central black and white squares. The processing circuitry receives respective images captured by the image sensor of the optical target at respective rotational positions of the optical target. The processing circuitry computes the optical-aberration correction for the image sensor responsively to the respective positions of the respective alignment features in the respective received images.

Various methods for correcting optical aberrations using a chessboard are described in the art. One such example is described in a paper entitled "A Robust Chessboard Detector for Geometric Camera Calibration" by Mathis Hoffmann, Andreas Ernst, Tobias Bergen, Sebastian Hettenkofer and Jens-Uwe Garbas of Fraunhofer Institute for Integrated Circuits IIS, Am Wolfsmantel 33, 91058 Erlangen, Germany.

In some embodiments, the magnetic field generator includes three calibration-coil sets (e.g., three Helmholtz coils) respectively aligned with three orthogonal axes of a magnetic coordinate frame. The magnetic field sensor may also include three position coils (e.g., a triple-axis magnetic sensor). In these embodiments, the processing circuitry actuates the calibration-coil sets to generate magnetic fields for detection by the position coils. The calibration-coil sets may be actuated one-by-one or simultaneously (if different respective frequencies are used for the respective calibration-coil sets). If the magnetic field sensor is a triple axis sensor with its coils perfectly aligned with the generated magnetic fields, there will only be a signal on one coil if only one Helmholtz coil is actuated. If there are signals on the other coils, the signals on these other coils are used by the processing circuitry to measure the misalignment of these other coils and thereby calibrate, for each of the position coils, the alignment with the magnetic coordinate frame responsively to signals received from position coils.

In some embodiments, the magnetic field sensor may include only one or only two position coils (e.g., a single-axis or a dual-axis magnetic sensor). In these embodiments, the processing circuitry calibrates the alignment of the single-axis or dual axis sensor with the generated magnetic field(s).

In some embodiments, the processing circuitry computes the sensitivity of the magnetic field sensor responsively to the signal(s) from the magnetic field sensor.

The processing circuitry stores the computed parameters (e.g., the alignment of the image sensor relative to the magnetic field sensor, the alignment of the magnetic field sensor to the generated magnetic field(s), and the sensitivity of the magnetic field sensor, and the optical aberration correction in a storage device (such as an electrically erasable programmable read-only memory (EEPROM)), typically comprised in the probe. The stored parameters may then be retrieved by a processing device during use of the probe to correct for misalignments of the magnetic field sensor, the image sensor, aberrations of the image sensor, and sensitivity mismatches of the magnetic field sensor.

System Description

Documents incorporated by reference herein are to be considered an integral part of the application except that, to the extent that any terms are defined in these incorporated documents in a manner that conflicts with definitions made explicitly or implicitly in the present specification, only the definitions in the present specification should be considered.

Figure 2:
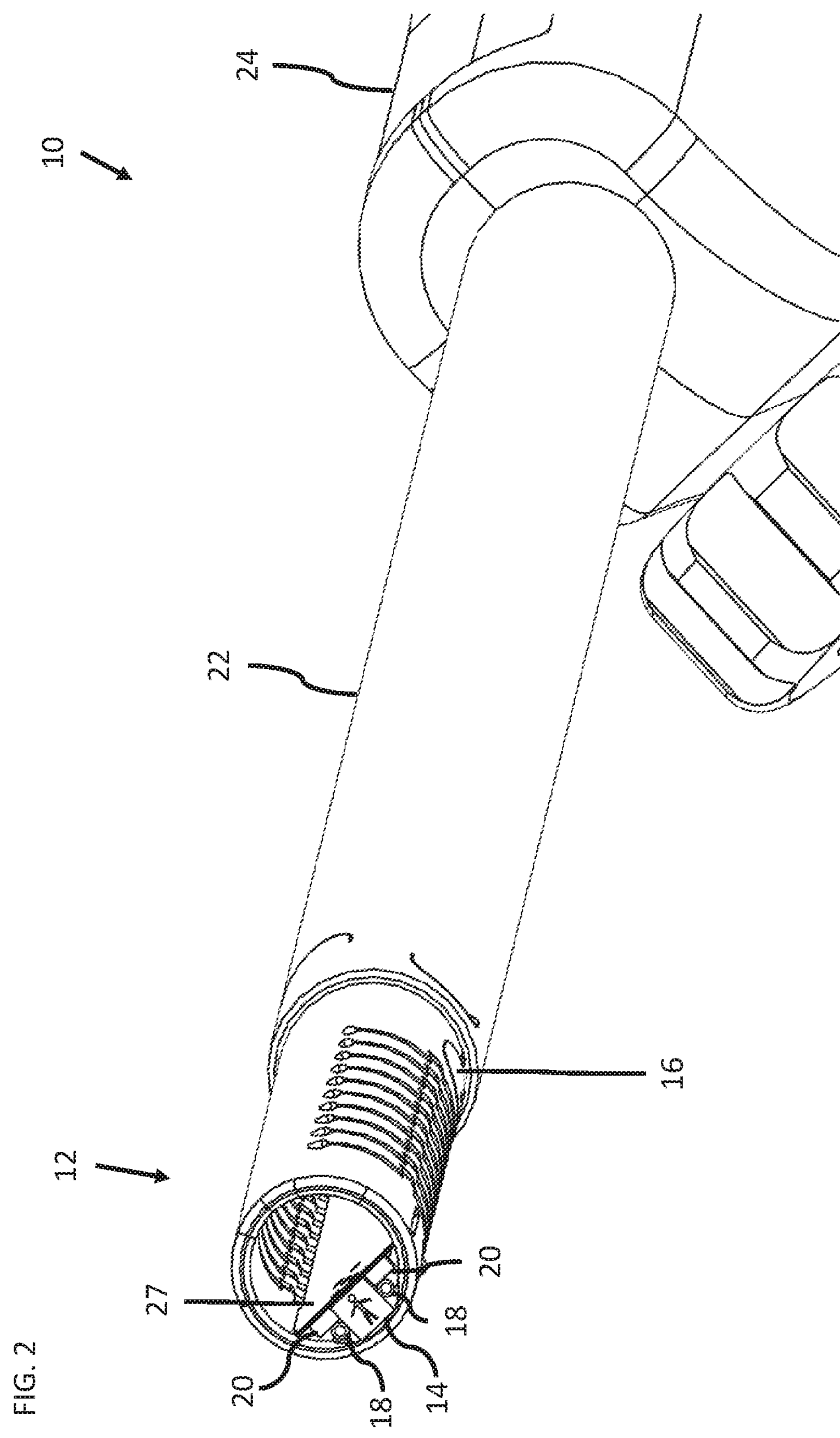
Figure 3:
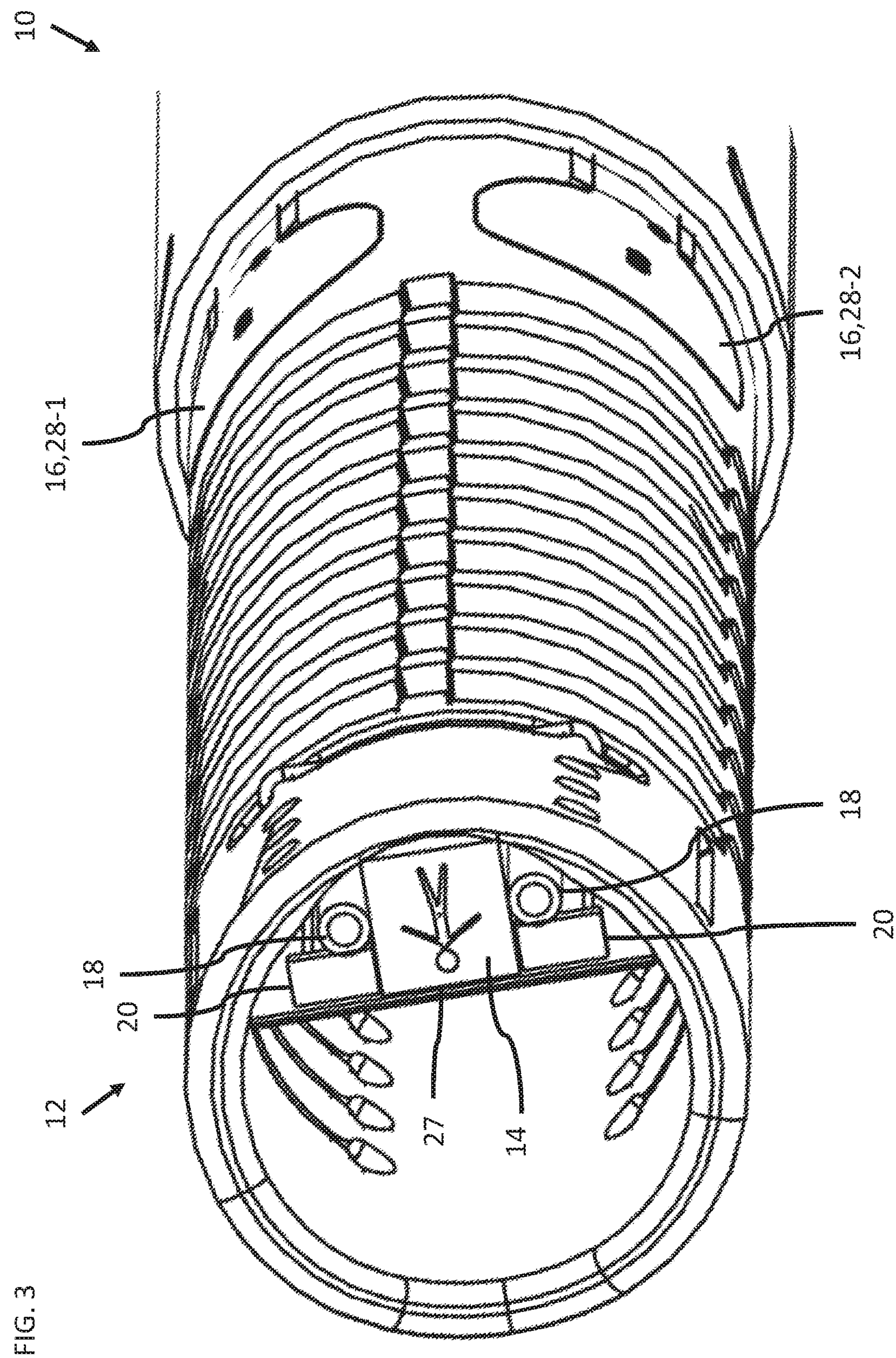

Reference is now made to FIGS. 1-3, which are schematic views of a probe 10 constructed and operative in accordance with an embodiment of the present invention. The probe 10 may be any suitable probe such as a catheter, guidewire, or a medical tool, e.g., an ENT tool. The probe 10 includes a distal end 12, a proximal end 22 (from which a guidewire extends, by way of example), and a handle 24, which allows an operator to control the probe 10 via various operating controls 26. The handle 24 may include a storage device 25, e.g., an EEPROM. The storage device 25 may be disposed in any suitable part of the probe 10, for example, but not limited to the proximal end 22. Use of the storage device is described in more detail with reference to FIG. 11.

Reference is now made to FIGS. 2 and 3. The distal end 12 includes an image sensor 14 (such as a camera) and a magnetic field sensor 16. The probe 10 may optionally include other elements such as one or more irrigation tubes (and/or suction tubes) 18, and one or more illuminating (lighting) elements 20, by way of example only. The distal end 12 may be deflectable. FIGS. 2 and 3 show that the image sensor 14, the illuminating elements 20 and the irrigation tubes 18 are connected directly or indirectly to a supporting strip 27, which is formed from any suitable deflectable and resilient material, for example, but not limited to nitinol or stainless steel.

The magnetic field sensor 16 may include multiple position coils 28, for example, two or three position coils. FIG. 3 shows two orthogonally disposed position coils 28-1, 28-2, disposed around a proximal portion of the distal end 12. The axis of each of the position coils 28-1, 28-2 is disposed perpendicular to the longitudinal axis of the probe. The position coils 28-1, 28-2 may be wound coils disposed inside the distal end 12, or printed circuit board (PCB) printed coils (for example, printed on flexible PCB) as shown in FIG. 3, or any other suitably placed coils. The position coils 28-1, 28-2, may be used to determine a position and/or orientation (roll) of the distal end 12.

Figure 4:
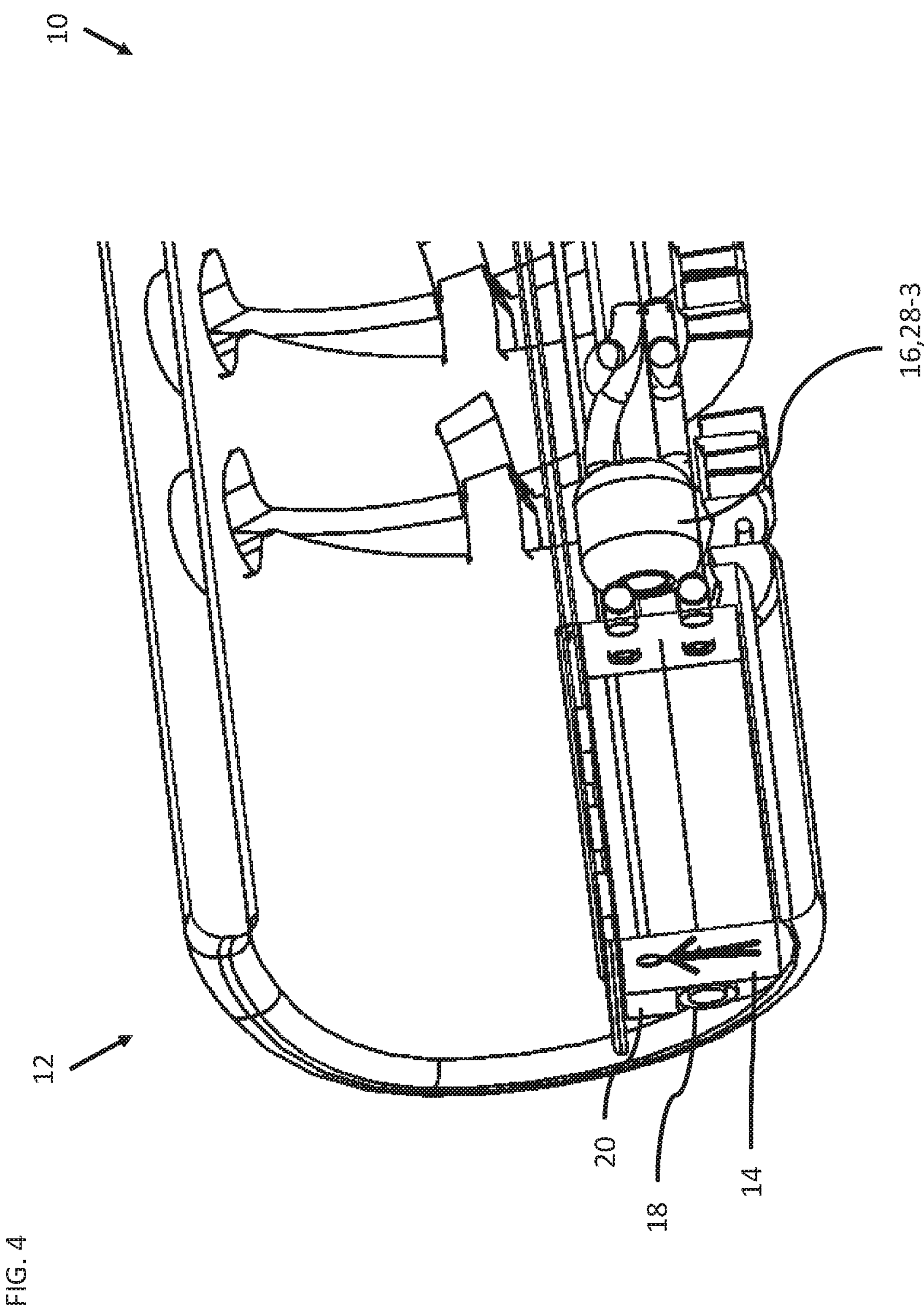
FIG. 4 is a cut-away view of the distal end of the probe of FIG. 1.

Reference is now made to FIG. 4, which is a cut-away view of the distal end 12 of the probe 10 of FIG. 1. FIG. 4 shows a third position coil 28-3 disposed proximally to the image sensor 14. The position coil 28-3 is disposed with its axis parallel to the longitudinal axis of the probe 10. The position coil 28-3 may be a wound coil or a PCB printed coil, by way of example only. The position coil 28-3 may be used to determine a position and/or orientation (excluding roll) of the distal end 12. It should be noted that the positioning of the position coils 28 is shown in the figures by way of example only. The position coils 28 may be disposed in the distal end 12 in any suitable position and/or orientation.

Figure 5:
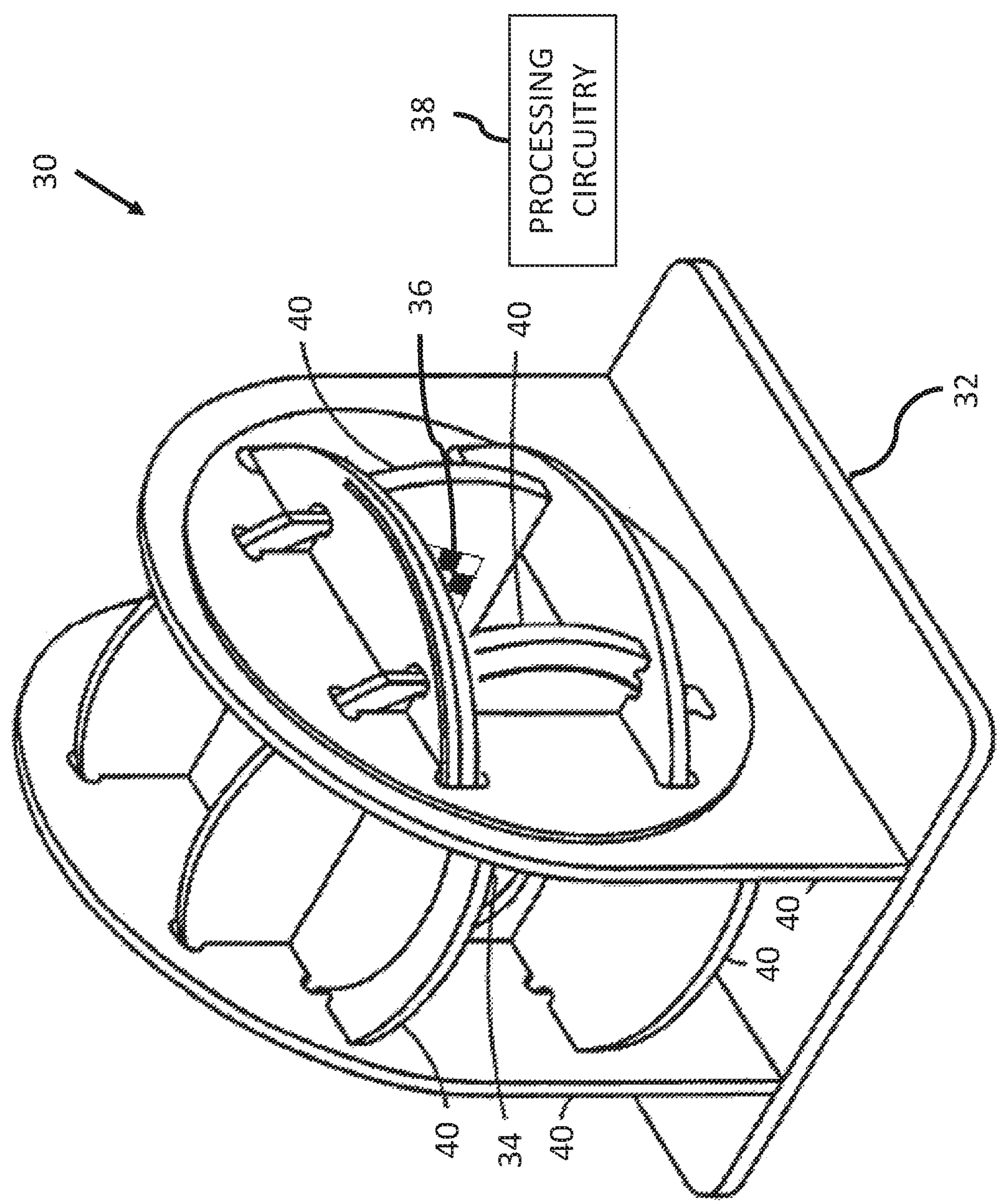
FIG. 5 is an isometric view of a calibration apparatus constructed and operative in accordance with an embodiment of the present invention.

Reference is now made to FIG. 5, which is an isometric view of a calibration apparatus 30 constructed and operative in accordance with an embodiment of the present invention. The calibration apparatus 30 includes a magnetic field generator 32, a jig 34, an optical target 36, and processing circuitry 38.

The magnetic field generator 32 is configured to generate at least one time-varying magnetic field having a predefined direction in alignment with the jig 34. In some embodiments the magnetic field generator 32 is configured to generate two or three magnetic fields corresponding to two or three orthogonal axes. Each of the magnetic fields is typically generated so as to generate a uniform magnetic field within the region of the jig 34.

In some embodiments, the magnetic field generator comprises three calibration-coil sets 40 respectively aligned with three orthogonal axes of a magnetic coordinate frame 44. In some embodiments, each of the calibration-coil sets 40 includes two coils, e.g., a Helmholtz coil which provides a uniform magnetic field. Helmholtz coil systems are commercially available, for example, from Bartington Instruments, Oxford, England).

The calibration-coil sets 40 are coupled to driver circuitry (not shown), which causes the calibration-coil sets 40 to generate magnetic fields. Each calibration-coil set 40 generates a magnetic field that is substantially normal to the planes defined by that calibration-coil set 40, and is thus substantially orthogonal to fields generated by the other two calibration-coil sets 40.

Each calibration-coil set 40 is configured so as to generate predetermined, substantially uniform magnetic fields in a region adjacent to the center of the jig 34, i.e., in a region of the three position coils 28 (FIGS. 3 and 4). The driver circuitry is adjusted so that the amplitudes of the respective magnetic fields generated by three calibration-coil sets 40 are equal.

The processing circuitry 38 is described below in more detail with reference to FIG. 11. In practice, some or all of the functions of the processing circuitry 38 may be combined in a single physical component or, alternatively, implemented using multiple physical components. These physical components may comprise hard-wired or programmable devices, or a combination of the two. In some embodiments, at least some of the functions of the processing circuitry may be carried out by a programmable processor under the control of suitable software. This software may be downloaded to a device in electronic form, over a network, for example. Alternatively, or additionally, the software may be stored in tangible, non-transitory computer-readable storage media, such as optical, magnetic, or electronic memory.

Figure 6:
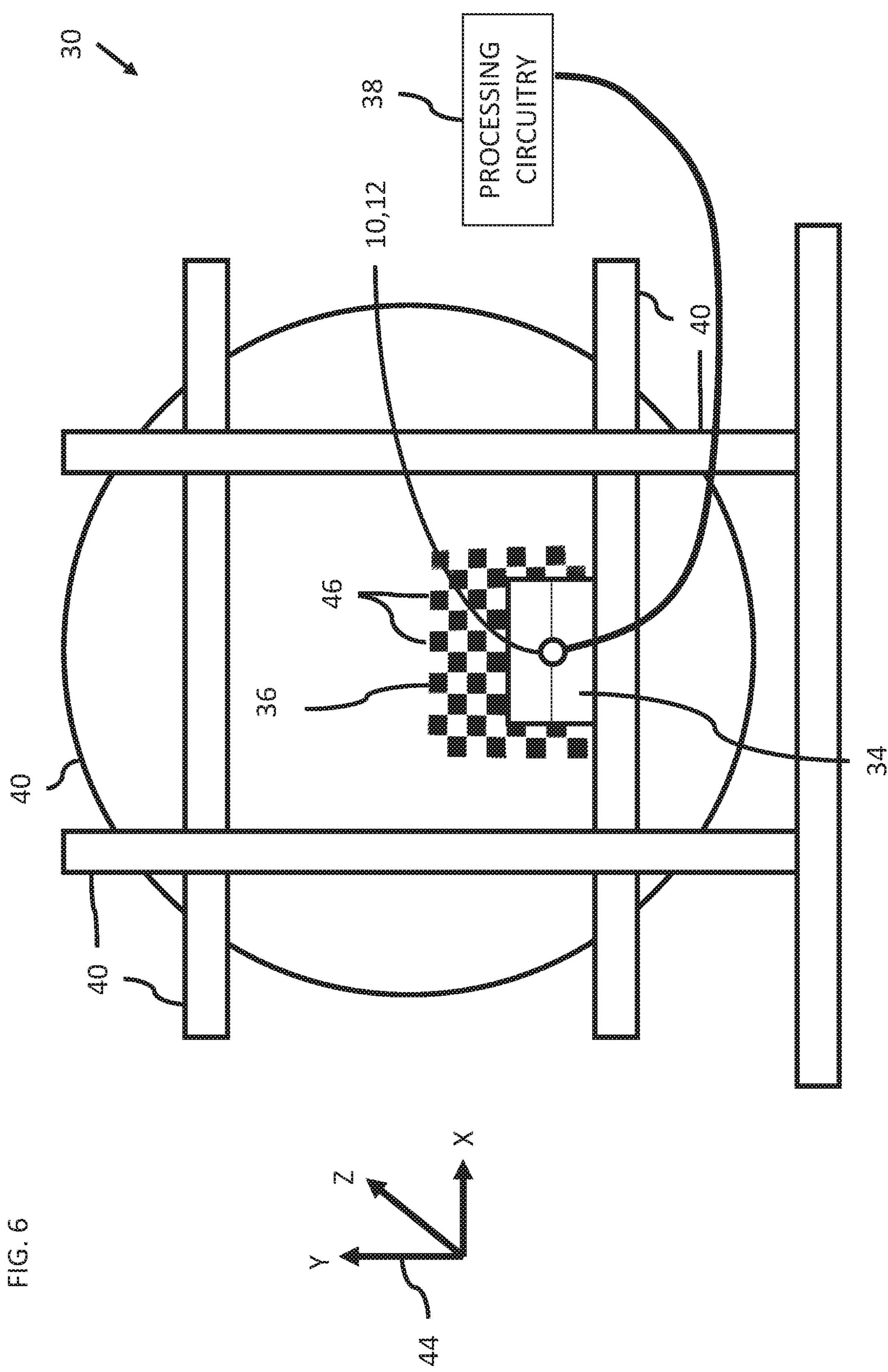
FIG. 6 is a front view of the calibration apparatus of FIG. 5.
Figure 7:
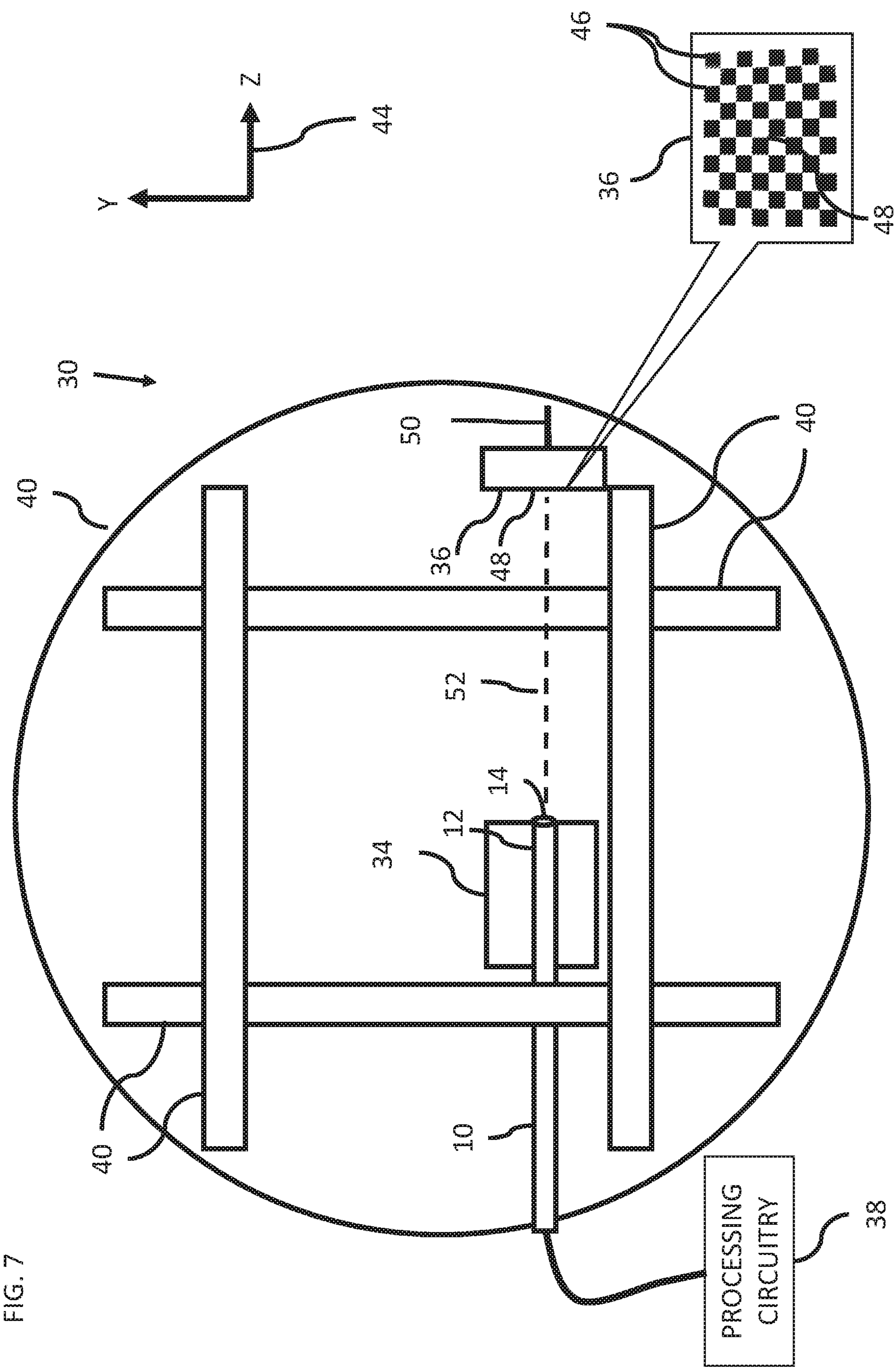
FIG. 7 is a side view of the calibration apparatus of FIG. 5.

Reference is now made to FIGS. 6 and 7. FIG. 6 is a front view of the calibration apparatus 30 of FIG. 5. FIG. 7 is a side view of the calibration apparatus 30 of FIG. 5.

The jig 34 is configured to hold the distal end 12 of the probe 10. The jig 34 is fixed to one of the calibration-coil sets 40 and is aligned with the axes of the magnetic coordinate frame 44. The jig 34 may include a clamp assembly constructed and configured so that the distal end 12 of the probe 10 is held in the jig 34 in the region of substantially uniform magnetic fields adjacent to the center of the jig 34, and so that the long axis of the probe 10 will be substantially normal to the planes defined by one of the calibration-coil sets 40. The jig 34 includes respective semi-circular grooves, whose radii are substantially equal to the outer radius of the distal end 12 probe 10.

The jig 34 may include a heating element (not shown) and at least one temperature sensor (not shown), which are used to heat distal end 12 of probe 10 to a temperature substantially equal to the temperature of the body into which the probe 10 is to be inserted, and to maintain the distal end 12 at that temperature during calibration. As is known in the art, the response of position coils 28 (FIGS. 3, 4) to magnetic fields may change as a function of temperature. For example, when the coils are wound around ferrite cores, their inductance may change with temperature, which can introduce errors into the calibration of the magnetic field sensor 16 (FIG. 3, 4). Therefore, distal end 12 is typically heated to and maintained at a temperature of 37° C. during calibration, although other temperatures may be chosen, for example when the probe 10 is to be used under conditions of hypothermia, such as are generally induced during open-heart surgery.

The probe 10 is inserted in the jig 34, and rotated about its long axis to a desired rotational orientation, wherein the axes of the position coils 28 (FIGS. 3 and 4) are substantially aligned with the respective axes of the magnetic coordinate frame 44 defined by the respective calibration-coil sets 40. The desired rotational orientation may be indicated, for example, by fiducial marks or other features (not shown in the figures) on the probe 10 outer surface. In this manner the probe 10 is fixed in a known orientation relative to the magnetic fields generated by the calibration-coil sets 40. The probe 10 is also connected to the processing circuitry 38.

The respective gains and angular orientations of the position coils 28 are then calibrated by sequentially activating the calibration-coil sets 40 to generate predetermined, known magnetic fields, and measuring the amplitudes of the signals generated by the position coils 28.

First, to calibrate the gains (sensitivity) of the position coils 28, total amplitudes of the respective position coil signals are derived by summing the squares of the amplitudes of the signals generated by each of position coils 28 in response to each of the calibration-coil sets 40 in turn. Since the magnetic fields in the vicinity of position coils 28 have equal and substantially uniform components along each of the axes of the position coils 28, the total signal amplitudes will be independent of the respective orientations and positions of the position coils 28, and will depend only on the respective coil gains. Thus, the measured total signal amplitudes may be used to determine respective normalization factors for position coils 28, by dividing the measured amplitudes by expected standard values. Subsequently the amplitudes of signals received from these coils may be multiplied by the respective normalization factors in order to correct for gain variations.

The normalized amplitude of the signal generated by each of the position coils 28 in response to each of the magnetic fields will be proportional to the cosine of the angle between the respective axis of the position coils 28, and the direction of the applied magnetic field. Three such angle cosines, corresponding to the directions of the three orthogonal magnetic fields applied by calibration-coil sets 40 may thus be derived for each of the position coils 28. Since as noted above, the probe 10 is held in the jig 34 in such a manner that the axes of the probe 10 are substantially aligned with the three orthogonal magnetic field directions of the magnetic coordinate frame 44, the orientations of the position coils 28 relative to the axes of the probe 10 may thus be determined.

In some embodiments of the present invention, when the Z-axis magnetic field is activated, a normalized amplitude of the signal received from the position coil 28-3 (FIG. 4) is received and measured. The X- and Y-axis fields are similarly activated, and corresponding normalized signals are received from the position coil 28-3. The received signals are used to calculate coil angle calibration factors for the position coil 28-3, which are thereafter recorded in the probe 10 and used in determining the probe's position and orientation. A similar procedure is used to calibrate coils 28-1, 28-2 (FIG. 3).

The optical target 36 is also aligned with the jig 34 so that the image sensor 14 in the probe 10 is able to capture an image of the optical target 36 while the probe 10 is held in the jig 34. The optical target 36 comprises multiple alignment features 46 (only some labeled for the sake of simplicity). In some embodiments, the optical target 36 includes multiple alternating rectangular (e.g., square) black and white (or darker and lighter) sections, similar to a chess or checker board. In other embodiments a single suitably shaped alignment feature, e.g., a cross, may be used instead of the chess board pattern. In other embodiments, other suitably shaped alignment features may be used.

In some embodiments, the alignment features 46 may include a central alignment feature 48 disposed substantially centrally in optical target 36 so that the central alignment feature 48 is substantially aligned (indicated with dotted line 52) with the X and Y position of a central longitudinal axis of the distal end 12 of the probe 10.

In some embodiments, the optical target 36 is configured to be rotated around the central alignment feature 48, for example, using a bearing 50, around the Z axis. The rotational motion of the optical target 36 may be controlled using a motor (not shown), which may be controlled by the processing circuitry 38. Respective images of the optical target 36 may be captured by the image sensor 14 at respective rotational positions of the optical target 36.

Calibration of the position and orientation of the image sensor 14 as well as correcting for optical aberrations is performed based on the captured image(s) as described in more detail with reference to FIGS. 8-11.

Figure 8:
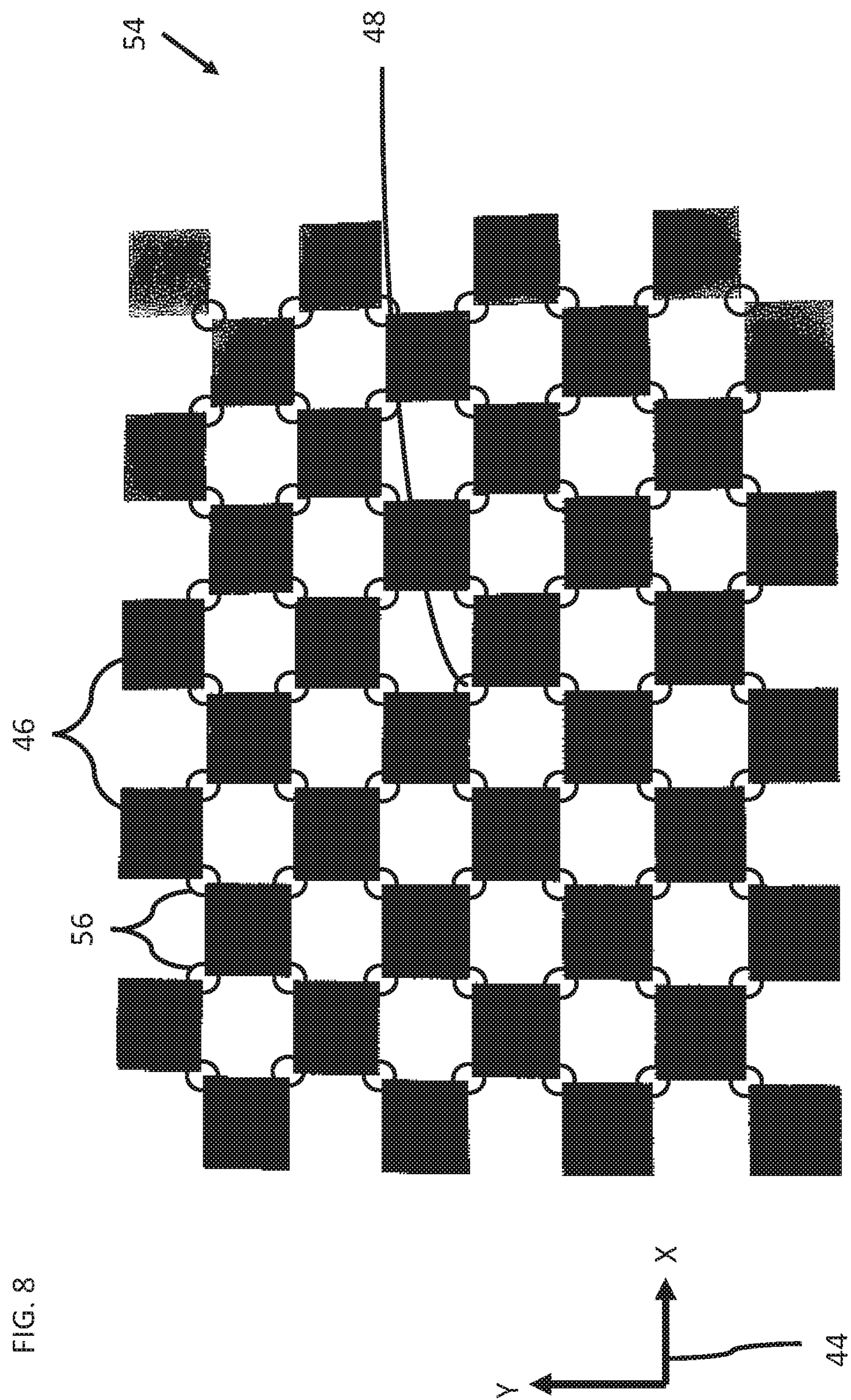
FIG. 8 is a schematic view of a captured image being analyzed in the apparatus of FIG. 5.

Reference is now made to FIG. 8, which is a schematic view of a captured image 54 being analyzed in the calibration apparatus 30 of FIG. 5.

The processing circuitry 38 (FIGS. 5-7) is configured to find respective boundaries between respective rectangular (e.g., square) sections corresponding with respective ones of the multiple alignment features 46 (only some labeled for the sake of simplicity) in the captured image 54, for example, but not limited to, using image processing techniques such as edge detection. Circles 56 (only some labeled for the sake of simplicity) are centered around the found boundaries (detected points) between the rectangular sections. The boundaries may be used to calibrate an alignment of the image sensor 14 (FIGS. 3, 4), for example with respect to the magnetic field sensor 16 (FIGS. 3, 4), based on: the position of the central alignment feature 48 in the captured image 54 and/or on the position and orientation of the alignment features 46 in the captured image 54; the given spatial relation between the alignment features 46 of the optical target 36 (FIGS. 6, 7) and the magnetic coordinate frame 44 (defined by the magnetic field generated by the calibration-coil sets 40 (FIGS. 6, 7)); the given spatial relation between the jig 34 (FIGS. 6, 7) and the alignment features 46 of the optical target 36; the optical characteristics of the image sensor 14; and optionally the alignment between the magnetic field sensor 16 and the magnetic coordinate frame 44. The calibration of the alignment of the image sensor 14 described above may be based on corrected positions of the alignment features 46 in the captured image 54 corrected for optical aberrations as described with reference to FIG. 9 below.

Figure 9:
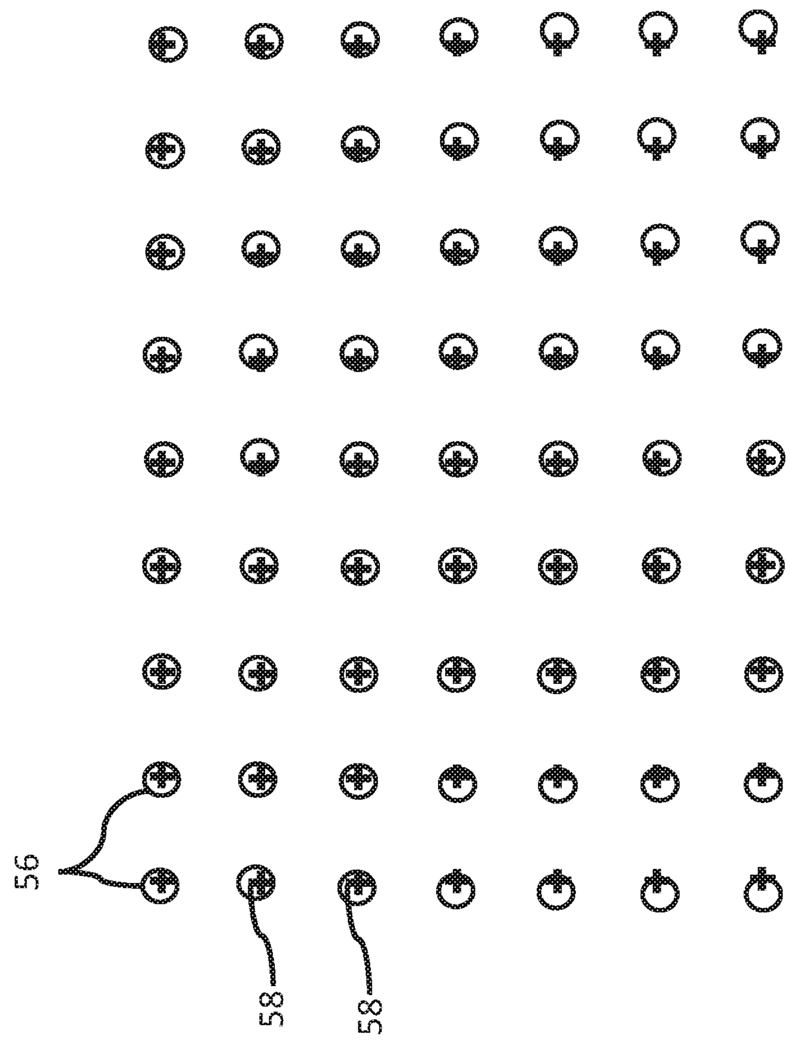
FIG. 9 is a schematic view illustrating a method of optical aberration correction in the apparatus of FIG. 5.

Reference is now made to FIG. 9, which is a schematic view illustrating a method of optical aberration correction in the calibration apparatus 30 of FIG. 5. As described above with reference to FIG. 8, circles 56 are centered around the boundaries between the rectangular sections of the alignment features 46 (FIG. 8). If the image sensor 14 was free of optical imperfections, the captured image 54 (FIG. 8) would include the alignment features 46 exactly as included on the optical target 36, with the correct positioning, spacing, and orientation. In particular, lines defined by the centers of the circles 56 (only some labeled for the sake of simplicity) would be straight, parallel, and equally spaced. Instead the lines defined by the centers of the circles 56 in FIG. 9 are not straight, parallel, and equally spaced. FIG. 9 also shows crosses 58 (only some labeled for the sake of simplicity), whose centers define straight, parallel, and equally spaced lines, based on the geometry of the alignment features 46 of the optical target 36. The pattern of the crosses 58 is centered around the center of the captured image 54. The displacement between the centers of respective circles 56 and the center of respective crosses 58 defines an optical-aberration (e.g., spherical aberration) correction for the image sensor 14 and may optionally be used to calibrate the alignment of the image sensor 14 with the magnetic field sensor 16. The above processing may be repeated for different rotation positions of the optical target 36. The rotation position of the optical target 36 does not need to be known by the processing circuitry 38 in order to perform the optical-aberration correction. Other optical aberration corrections, such as chromatic aberration correction, may be computed using methods known to those skilled in the art based on suitable analysis of the captured image 54.

Figure 10:
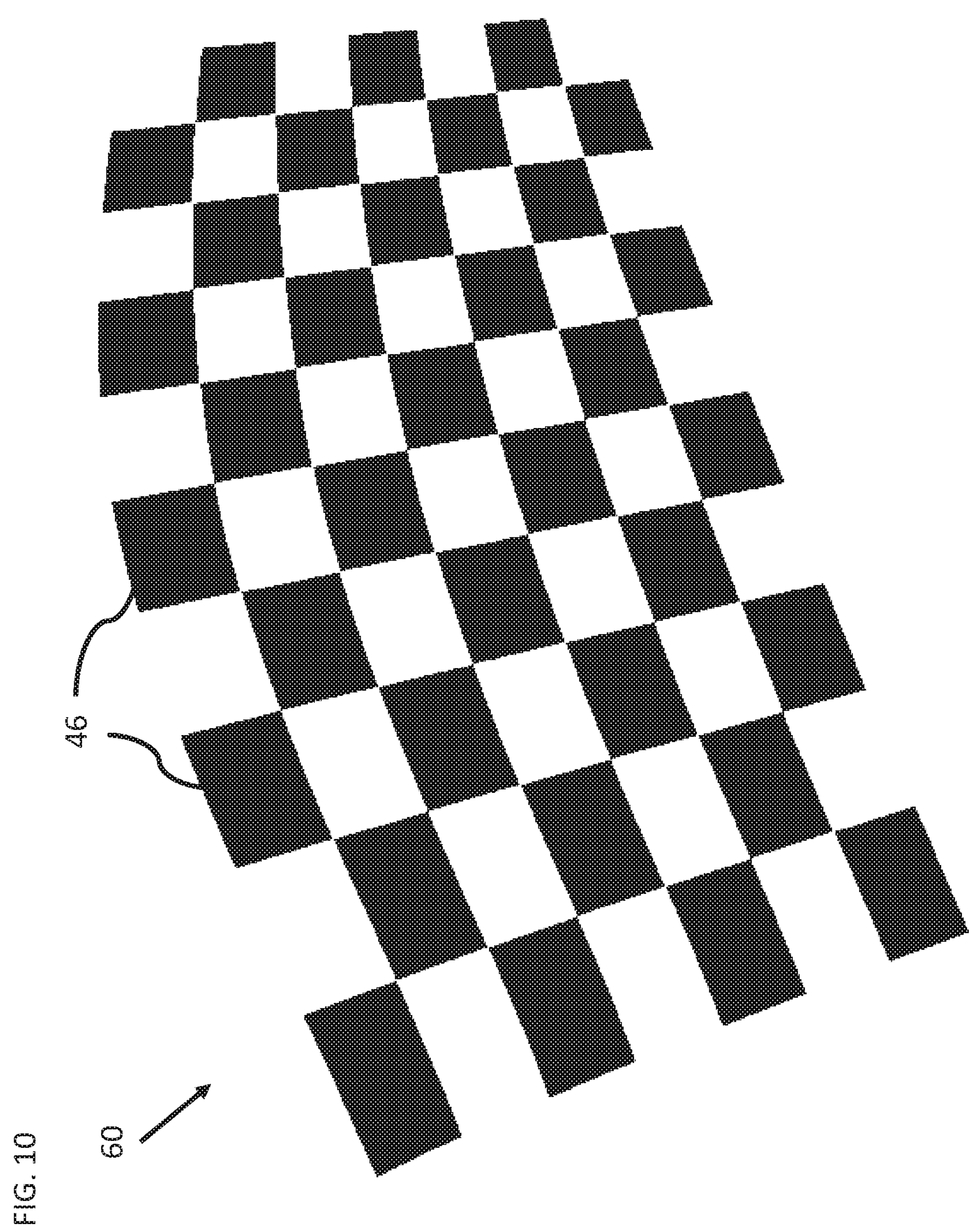
FIG. 10 is a schematic view of another captured image in the apparatus of FIG. 5.

Reference is now made to FIG. 10, which is a schematic view of another captured image 60 in the calibration apparatus 30 of FIG. 5. The captured image 60 was captured when the optical target 36 was rotated so that the sides of the optical target 36 are not aligned with the X and Y axis of the magnetic coordinate frame 44 (FIGS. 6, 7). The captured image 60 clearly shows that the lines defined by the alignment features 46 are not straight, parallel, and equally spaced lines, and therefore, the image sensor 14 is exhibiting spherical aberrations.

Figure 11:
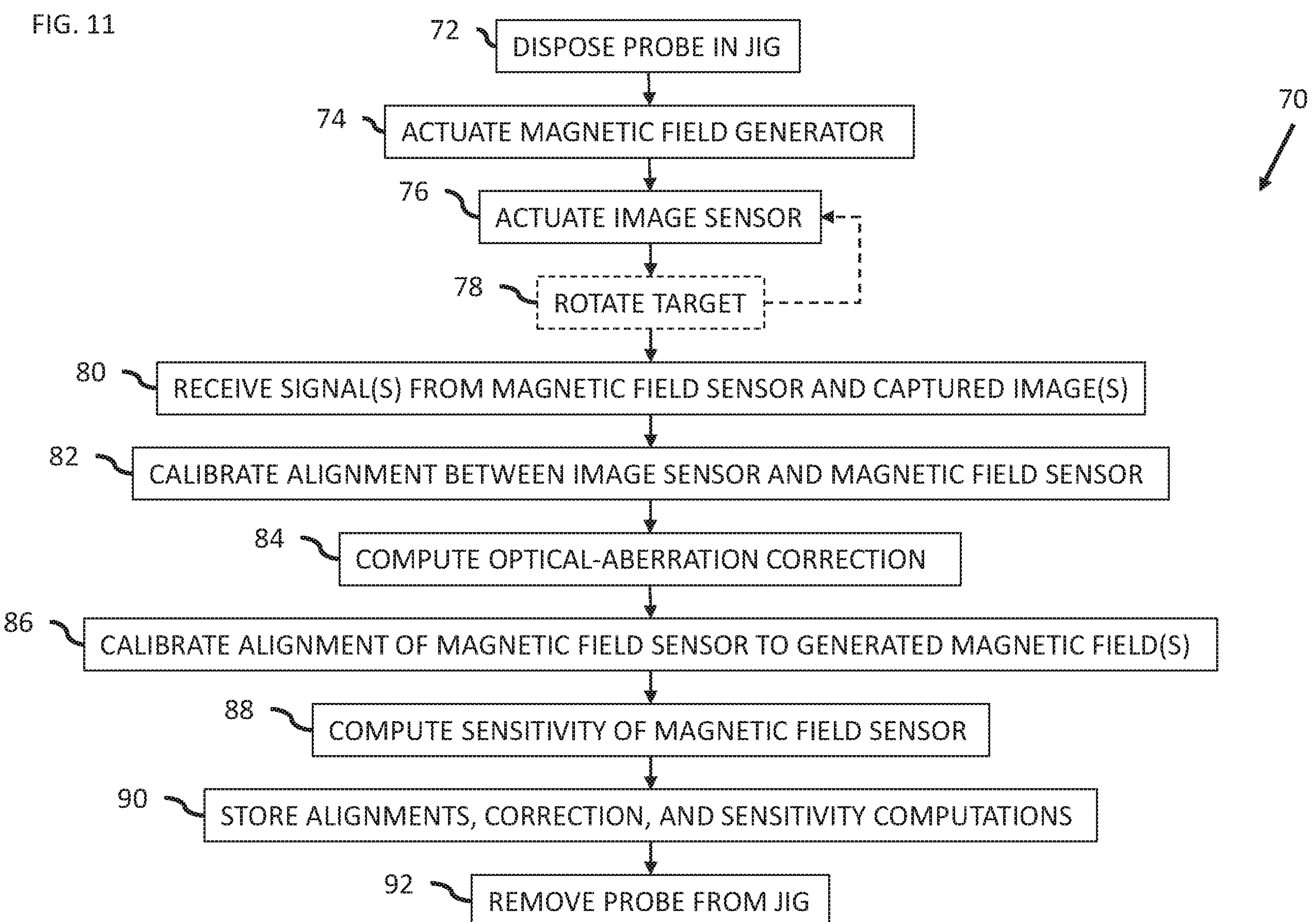
FIG. 11 is a flowchart including steps in a method of operation in the apparatus of FIG. 5.

Reference is now made to FIG. 11, which is a flowchart 70 including steps in a method of operation in the calibration apparatus 30 of FIG. 5. Reference is also made to FIGS. 6 and 7.

The probe 10 is disposed (block 72) in the jig 34 as described above with reference to FIGS. 6 and 7. The processing circuitry 38 is configured to actuate (block 74) the calibration-coil sets 40 of the magnetic field generator 32 to generate magnetic fields using the calibration-coil sets 40. The generated magnetic fields are detected by the position coils 28 (FIGS. 3 and 4) while the probe 10 is held in the jig 34. The calibration-coil sets 40 may be actuated in turn as described above with reference to FIG. 6 or 7, or the calibration-coil sets 40 may be actuated simultaneously if different respective frequencies are used for different respective calibration-coil sets 40 (i.e., a first calibration-coil set 40 generates a first frequency, a second calibration-coil set 40 generates a second frequency, and a third calibration-coil set 40 generates a third frequency).

The processing circuitry 38 is configured to actuate (block 76) the image sensor 14 of the probe 10 to capture an image of the optical target 36 while the probe 10 is held in the jig 34.

The processing circuitry 38 is optionally configured to actuate a motor (not shown) to rotate (block 78) the optical target 36 to a new rotational position. The step of block 76 is repeated at the new rotational position. The steps of blocks 76 and 78 may be repeated any suitable number of times. Increasing the number of images used in calibrating the image sensor 14 may improve an accuracy of the calibration of the image sensor 14.

The processing circuitry 38 is configured to receive (block 80) from the probe: a signal (or signals) output by the magnetic field sensor 16 (from the position coils 28) in response to the magnetic field(s); and the image(s) captured by the image sensor 14 of the optical target 36 (e.g., at multiple respective rotational positions of the optical target 36), while the probe 10 is held in the jig 34.

Each received image includes at least some alignment features of the multiple alignment features 46. In some embodiments, the processing circuitry 38 is configured to find respective boundaries between respective rectangular sections corresponding with respective ones of the multiple alignment features 46, as described above with reference to FIG. 8. A central boundary between ones of the rectangular sections corresponds with the central alignment feature 48.

The processing circuitry 38 is configured to calibrate (block 82) an alignment of the image sensor 14 relative to the magnetic field sensor 16 responsively to the received signal, the received image, and other factors, for example, but not limited to, the position of the central alignment feature 48 in the captured image 54 (FIG. 8) and/or on the position and orientation of the alignment features 46 in the captured image 54, the given spatial relation between the alignment features 46 of the optical target 36 and the magnetic coordinate frame 44 (defined by the magnetic fields generated by the calibration-coil sets 40), the given spatial relation between the jig 34 and the alignment features 46 of the optical target 36, the optical characteristics of the image sensor 14, and optionally the alignment between the magnetic field sensor 16 and the magnetic coordinate frame 44. The calibration of the alignment of the image sensor 14 described above may be based on corrected positions of the alignment features 46 in the captured image 54 corrected for optical aberrations as described below and with reference to FIG. 9.

The processing circuitry 38 is configured to compute (block 84) an optical-aberration correction for the image sensor 14 responsively to respective positions of respective ones of the at least some alignment features 46 in the received image. In some embodiments, the processing circuitry 38 is configured to compute the optical-aberration correction for the image sensor responsively to a curvature of at least one line defined by the respective positions of respective ones of the at least some alignment features 46 in the received image.

In some embodiments, when multiple respective images are captured at multiple rotational positions of the optical target 36, the processing circuitry 38 is configured to compute the optical-aberration correction for the image sensor 14 responsively to the respective positions of respective ones of the alignment features 46 in the respective received images.

The processing circuitry is configured to calibrate (block 86) an alignment of the magnetic field sensor 16 to the magnetic field(s) generated by the magnetic field generator 32 responsively to the received signal(s) from the magnetic field sensor 16, as described above in more detail with reference to FIGS. 6 and 7. In some embodiments, the processing circuitry 38 is configured to calibrate, for each of the position coils 28 (FIGS. 3, 4), an alignment with the magnetic coordinate frame 44 responsively to signals received from position coils 28.

The processing circuitry 38 is configured to compute (block 88) a sensitivity of the magnetic field sensor 16 responsively to the received signal(s) from the magnetic field sensor 16, as described in more detail with reference to FIGS. 6 and 7.

The processing circuitry is configured to store (block 90) the alignment of the image sensor 14 relative to the magnetic field sensor 16, the alignment of the magnetic field sensor 16 to the magnetic field(s) generated by the magnetic field generator 32, and the sensitivity of the magnetic field sensor 16, in the storage device 25 (FIG. 1) comprised in the probe 10.

The probe 10 is then removed (block 92) from the jig 34.

The software components of the present invention may, if desired, be implemented in ROM (read only memory) form. The software components may, generally, be implemented in hardware, if desired, using conventional techniques. The software components may be instantiated, for example: as a computer program product or on a tangible medium. In some cases, it may be possible to instantiate the software components as a signal interpretable by an appropriate computer, although such an instantiation may be excluded in certain embodiments of the present invention.

Various features of the invention which are, for clarity, described in the contexts of separate embodiments may also be provided in combination in a single embodiment. Conversely, various features of the invention which are, for brevity, described in the context of a single embodiment may also be provided separately or in any suitable sub-combination.

The embodiments described above are cited by way of example, and the present invention is not limited by what has been particularly shown and described hereinabove. Rather the scope of the invention includes both combinations and subcombinations of the various features described hereinabove, as well as variations and modifications thereof which would occur to persons skilled in the art upon reading the foregoing description and which are not disclosed in the prior art.

What is claimed is:

1. An apparatus for calibrating a probe that includes an image sensor and a magnetic field sensor, the apparatus comprising:

a magnetic field generator being configured to generate at least one magnetic field having a predefined direction in alignment with a jig;

the jig being configured to hold the probe such that the axes of the magnetic field sensor are substantially aligned with the respective axes of the magnetic coordinate frame based on the predefined direction of the magnetic field;

an optical target aligned with the jig, based on a central alignment feature, so that the image sensor in the probe is able to capture an image of the optical target while the probe is held in the jig, the optical target being configured to be rotated around the central alignment feature; and processing circuitry configured to receive from the probe a signal output by the magnetic field sensor in response to the at least one magnetic field and the image captured by the image sensor while the probe is held in the jig, and to calibrate an alignment of the image sensor relative to the magnetic field sensor responsively to the received signal and the received image.

2. The apparatus according to claim 1, the processing circuitry being configured to calibrate an alignment of the magnetic field sensor to the at least one magnetic field generated by the magnetic field generator responsively to the received signal.

3. The apparatus according to claim 2, the processing circuitry being configured to store the alignment of the image sensor relative to the magnetic field sensor and the alignment of the magnetic field sensor to the at least one magnetic field in a storage device comprised in the probe.

4. The apparatus according to claim 1, the processing circuitry being configured to compute a sensitivity of the magnetic field sensor responsively to the received signal.

5. The apparatus according to claim 1, the optical target comprising multiple alignment features; the received image includes at least some alignment features of the multiple alignment features; and the processing circuitry being configured to compute an optical-aberration correction for the image sensor responsively to respective positions of respective ones of the at least some alignment features in the received image.

6. The apparatus according to claim 5, the processing circuitry being configured to compute the optical-aberration correction for the image sensor responsively to a curvature of at least one line defined by the respective positions of respective ones of the at least some alignment features in the received image.

7. The apparatus according to claim 6, the optical target including multiple alternating rectangular sections; and the processing circuitry being configured to find respective boundaries between respective ones of the rectangular sections corresponding with respective ones of the multiple alignment features.

8. The apparatus according to claim 7, a central boundary between ones of the rectangular sections corresponding with the central alignment feature of the multiple alignment features, the processing circuitry being configured to calibrate the alignment of the image sensor relative to the magnetic field sensor responsively to the position of the central alignment feature in the received image.

9. The apparatus according to claim 8, the processing circuitry being configured to:
- receive a plurality of respective images captured by the image sensor of the optical target at multiple respective rotational positions of the optical target; and
- compute the optical-aberration correction for the image sensor responsively to the respective positions of respective ones of the at least some alignment features in the received respective images.

10. The apparatus according to claim 1,
- the magnetic field generator comprising three calibration-coil sets respectively aligned with three orthogonal axes of a magnetic coordinate frame;
- the magnetic field sensor including three position coils; and
- the processing circuitry being configured to:
  - actuate the calibration-coil sets to generate magnetic fields for detection by the position coils; and
  - calibrate, for each of the position coils, an alignment with the magnetic coordinate frame responsively to signals received from position coils.

11. A method for calibrating a probe that includes an image sensor and a magnetic field sensor, the method comprising:
- disposing the probe in a jig;
- generating at least one magnetic field having a predefined direction in alignment with the jig;
- rotating an optical target relative to the probe and a portion of the jig;
- capturing with the image sensor an image of the optical target aligned with the jig while the probe is held stationary in the jig,
- receiving from the probe a signal output by the magnetic field sensor in response to the at least one magnetic field and the image captured by the image sensor while the probe is held in the jig; and
- calibrating an alignment of the image sensor relative to the magnetic field sensor responsively to the received signal and the received image.

12. The method according to claim 11, further comprising calibrating an alignment of the magnetic field sensor to the at least one magnetic field responsively to the received signal.

13. The method according to claim 12, further comprising storing the alignment of the image sensor relative to the magnetic field sensor and the alignment of the magnetic field sensor to the at least one magnetic field in a storage device comprised in the probe.

14. The method according to claim 11, further comprising computing a sensitivity of the magnetic field sensor responsively to the received signal.

15. The method according to claim 11, the optical target comprising multiple alignment features; the received image including at least some alignment features of the multiple alignment features; and the method further comprising computing an optical-aberration correction for the image sensor responsively to respective positions of respective ones of the at least some alignment features in the received image.

16. The method according to claim 15, the computing of the optical-aberration correction being performed responsively to a curvature of at least one line defined by the respective positions of respective ones of the at least some alignment features in the received image.

17. The method according to claim 16, the optical target including multiple alternating rectangular sections; and the method further comprises finding respective boundaries between respective ones of the rectangular sections corresponding with respective ones of the multiple alignment features.

18. The method according to claim 17, a central boundary between ones of the rectangular sections corresponding with a central alignment feature of the multiple alignment features; and calibrating the alignment of the image sensor relative to the magnetic field sensor being performed responsively to the position of the central alignment feature in the received image.

19. The method according to claim 18, further comprising:
- rotating the optical target around the central alignment feature to multiple rotational positions; and
- receiving a plurality of respective images captured by the image sensor of the optical target at respective ones of the multiple rotational positions of the optical target, and the computing the optical-aberration correction for the image sensor being performed responsively to the respective positions of respective ones of the at least some alignment features in the received respective images.

20. The method according to claim 11, further comprising:
- actuating three calibration-coil sets respectively aligned with three orthogonal axes of a magnetic coordinate frame to generate magnetic fields for detection by three position coils of the magnetic field sensor; and
- calibrating, for each of the position coils, an alignment with the magnetic coordinate frame responsively to signals received from position coils.

21. A method for using an apparatus to calibrate a probe, the probe comprising an image sensor and a magnetic field sensor, the apparatus comprising:
- a jig;
- a magnetic field generator;

an optical target aligned with the jig, based on a central alignment feature, the optical target being configured to be rotated around the central alignment feature; and processing circuitry;

the method comprising:

disposing the probe in the jig;

generating at least one magnetic field having a predefined direction in alignment with the jig, the jig holding the probe such that the axes of the magnetic field sensor are substantially aligned with the respective axes of the magnetic coordinate frame based on the predefined direction of the at least one magnetic field;

capturing with the image sensor the image of the optical target aligned with the jig while the probe is held stationary in the jig;

receiving from the probe the signal output by the magnetic field sensor in response to the at least one magnetic field and the image captured by the image sensor while the probe is held in the jig, the signal being received by the processing circuitry; and calibrating the alignment of the image sensor relative to the magnetic field sensor responsively to the received signal and the captured image, the calibrating being performed by the processing circuitry.

* * * * *